US012059980B2

(12) United States Patent
Migneco et al.

(10) Patent No.: US 12,059,980 B2
(45) Date of Patent: Aug. 13, 2024

(54) SEAT SYSTEM AND METHOD OF CONTROL

(71) Applicant: Lear Corporation, Southfield, MI (US)

(72) Inventors: Francesco Migneco, Saline, MI (US); David Gallagher, Sterling Heights, MI (US)

(73) Assignee: LEAR CORPORATION, Southfield, MI (US)

( * ) Notice: Subject to any disclaimer, the term of this patent is extended or adjusted under 35 U.S.C. 154(b) by 767 days.

(21) Appl. No.: 16/448,306

(22) Filed: Jun. 21, 2019

(65) Prior Publication Data

US 2020/0398700 A1    Dec. 24, 2020

(51) Int. Cl.
| | |
|---|---|
| *A61B 5/18* | (2006.01) |
| *A61B 5/00* | (2006.01) |
| *A61B 5/0205* | (2006.01) |
| *A61B 5/16* | (2006.01) |
| *B60N 2/02* | (2006.01) |
| *B60Q 9/00* | (2006.01) |
| *A61B 5/024* | (2006.01) |
| *A61B 5/08* | (2006.01) |
| *B60N 2/20* | (2006.01) |

(52) U.S. Cl.
CPC .......... *B60N 2/0244* (2013.01); *A61B 5/0205* (2013.01); *A61B 5/165* (2013.01); *A61B 5/18* (2013.01); *A61B 5/6893* (2013.01); *B60Q 9/00* (2013.01); *A61B 5/02405* (2013.01); *A61B 5/0816* (2013.01); *B60N 2/20* (2013.01)

(58) Field of Classification Search
CPC . A61B 5/0205; A61B 5/02405; A61B 5/0816; A61B 5/165; A61B 5/18; A61B 5/6893; B60N 2002/981; B60N 2/002; B60N 2/0244; B60N 2/20; B60Q 9/00
USPC ......................................................... 701/49
See application file for complete search history.

(56) References Cited

U.S. PATENT DOCUMENTS

| | | | |
|---|---|---|---|
| 5,694,939 | A | 12/1997 | Cowings |
| 5,807,114 | A | 9/1998 | Hodges et al. |
| 6,366,207 | B1 | 4/2002 | Murphy |
| 6,438,399 | B1 | 8/2002 | Kurth |
| 7,138,922 | B2 | 11/2006 | Strumolo et al. |
| 7,431,120 | B2 | 10/2008 | Pollehn et al. |

(Continued)

FOREIGN PATENT DOCUMENTS

| | | |
|---|---|---|
| CN | 102254403 A | 11/2011 |
| CN | 103043057 A | 4/2013 |

(Continued)

OTHER PUBLICATIONS

Shaffer et al., An Overview of Heart Rate Variability Metrics and Norms, published online Sep. 28, 2017, 51 pages, «https://www.ncbi.nlm.nih.gov/pmc/articles/PMC5624990».

(Continued)

*Primary Examiner* — Naomi J Small
(74) *Attorney, Agent, or Firm* — Brooks Kushman, P.C.

(57) ABSTRACT

A method of controlling a seat system. A physiological condition of the seat occupant may be assessed based on at least two of the heart rate, breathing rate, and heart rate variability. A countermeasure may be executed to alter the physiological condition of the seat occupant and/or data associated with the heart rate, breathing rate, and/or heart rate variability may be communicated.

19 Claims, 3 Drawing Sheets

(56) References Cited

U.S. PATENT DOCUMENTS

| | | |
|---|---|---|
| 7,437,219 B2 | 10/2008 | Bos |
| 7,774,052 B2 | 8/2010 | Burton et al. |
| 8,698,639 B2 | 4/2014 | Fung et al. |
| 8,706,204 B2 | 4/2014 | Seo et al. |
| 8,903,494 B2 | 12/2014 | Goldwasser et al. |
| 8,941,499 B2 | 1/2015 | Fung et al. |
| 9,002,458 B2 | 4/2015 | Pal et al. |
| 9,014,811 B2 | 4/2015 | Pal et al. |
| 9,124,955 B2 | 9/2015 | Geva et al. |
| 9,135,803 B1 | 9/2015 | Fields et al. |
| 9,149,236 B2 | 10/2015 | Chun et al. |
| 9,159,232 B2 | 10/2015 | Ricci |
| 9,233,244 B2 | 1/2016 | Pal et al. |
| 9,272,689 B2 | 3/2016 | Fung et al. |
| 9,298,985 B2 | 3/2016 | Krueger |
| 9,302,584 B2 | 4/2016 | Walsh et al. |
| 9,389,595 B2 | 7/2016 | Caskey et al. |
| 9,440,646 B2 | 9/2016 | Fung et al. |
| 9,454,887 B1 | 9/2016 | Matalgah |
| 9,460,601 B2 | 10/2016 | Mimar |
| 9,463,794 B1 | 10/2016 | Silver et al. |
| 9,475,502 B2 | 10/2016 | Fung et al. |
| 9,536,411 B2 | 1/2017 | Foley et al. |
| 9,539,944 B2 | 1/2017 | Tzirkel-Hancock et al. |
| 9,712,736 B2 | 7/2017 | Kearns et al. |
| 9,848,814 B2 | 12/2017 | Benson et al. |
| 9,956,963 B2 | 5/2018 | Vijaya Kumar et al. |
| 10,054,443 B1 | 8/2018 | Patel et al. |
| 10,210,409 B1 | 2/2019 | Migneco et al. |
| 10,246,102 B2 | 4/2019 | Graney |
| 10,379,535 B2 | 8/2019 | Migneco et al. |
| 10,425,459 B2 | 9/2019 | Rider et al. |
| 10,836,403 B2 | 11/2020 | Migneco et al. |
| 10,867,218 B2 | 12/2020 | Gallagher et al. |
| 2005/0022606 A1 | 2/2005 | Partin et al. |
| 2005/0131607 A1 | 6/2005 | Breed |
| 2006/0015000 A1 | 1/2006 | Kim |
| 2007/0156295 A1 | 7/2007 | Stephane |
| 2008/0252466 A1* | 10/2008 | Yopp ............... B60K 28/066 340/576 |
| 2009/0174573 A1 | 7/2009 | Smith |
| 2009/0268022 A1 | 10/2009 | Omi |
| 2011/0144513 A1* | 6/2011 | Deluz ............... A61B 5/02405 600/519 |
| 2012/0116198 A1 | 5/2012 | Veen et al. |
| 2012/0150430 A1 | 6/2012 | French et al. |
| 2012/0259181 A1 | 10/2012 | Fujita et al. |
| 2012/0265262 A1 | 10/2012 | Osorio |
| 2012/0330173 A1 | 12/2012 | Park et al. |
| 2013/0054090 A1 | 2/2013 | Shin et al. |
| 2013/0088369 A1 | 4/2013 | Yu et al. |
| 2013/0204153 A1 | 8/2013 | Buzhardt |
| 2013/0325202 A1 | 12/2013 | Howard et al. |
| 2014/0136450 A1 | 5/2014 | Lee |
| 2014/0139655 A1 | 5/2014 | Mimar |
| 2014/0188920 A1 | 7/2014 | Sharma et al. |
| 2014/0221781 A1* | 8/2014 | Schrauf ............... B60K 28/06 600/301 |
| 2015/0008710 A1 | 1/2015 | Young et al. |
| 2015/0032382 A1 | 1/2015 | Lee et al. |
| 2015/0245777 A1 | 9/2015 | Della Torre et al. |
| 2015/0313475 A1* | 11/2015 | Benson ............... A61B 5/14552 600/323 |
| 2015/0328985 A1 | 11/2015 | Kim et al. |
| 2015/0360608 A1 | 12/2015 | Tzirkel-Hancock et al. |
| 2015/0379362 A1 | 12/2015 | Calmes et al. |
| 2016/0001781 A1 | 1/2016 | Fung et al. |
| 2016/0090097 A1 | 3/2016 | Grube et al. |
| 2016/0096412 A1 | 4/2016 | Mankame et al. |
| 2016/0133151 A1 | 5/2016 | O'Dowd et al. |
| 2016/0260343 A1 | 9/2016 | Resl |
| 2016/0285938 A1 | 9/2016 | Rider et al. |
| 2016/0287168 A1* | 10/2016 | Patel ............... A61B 5/1118 |
| 2016/0292988 A1 | 10/2016 | McCleary et al. |
| 2016/0354027 A1 | 12/2016 | Benson et al. |
| 2016/0362118 A1 | 12/2016 | Mollicone et al. |
| 2016/0378112 A1 | 12/2016 | Ljubuncic et al. |
| 2017/0068245 A1 | 3/2017 | Scofield et al. |
| 2017/0071525 A1 | 3/2017 | Lin et al. |
| 2017/0083757 A1 | 3/2017 | Enomoto et al. |
| 2017/0136842 A1 | 5/2017 | Anderson et al. |
| 2017/0188927 A1 | 7/2017 | Nakashima et al. |
| 2017/0196497 A1 | 7/2017 | Ray et al. |
| 2017/0267170 A1 | 9/2017 | Be et al. |
| 2017/0278122 A1 | 9/2017 | Kaehler |
| 2017/0311831 A1 | 11/2017 | Freer et al. |
| 2017/0349061 A1* | 12/2017 | Benson ............... B60N 2/1615 |
| 2017/0351812 A1 | 12/2017 | Green et al. |
| 2017/0355377 A1 | 12/2017 | Vijaya Kumar et al. |
| 2017/0360363 A1 | 12/2017 | Fonseca et al. |
| 2017/0367635 A1 | 12/2017 | Hur et al. |
| 2017/0367651 A1 | 12/2017 | Tzvieli |
| 2017/0370732 A1 | 12/2017 | Bender et al. |
| 2018/0008145 A1 | 1/2018 | Freer et al. |
| 2018/0015825 A1* | 1/2018 | Nania ............... G08B 21/06 |
| 2018/0134116 A1 | 5/2018 | Chen et al. |
| 2018/0136191 A1 | 5/2018 | Asvadi et al. |
| 2018/0143006 A1 | 5/2018 | White |
| 2018/0189681 A1 | 7/2018 | Harrivel et al. |
| 2018/0197636 A1 | 7/2018 | Firminger et al. |
| 2018/0229674 A1* | 8/2018 | Heinrich ............... A61B 5/18 |
| 2018/0263545 A1* | 9/2018 | Camporesi ............ A61B 5/165 |
| 2018/0276362 A1 | 9/2018 | Baughman et al. |
| 2018/0348740 A1 | 12/2018 | Rocci et al. |
| 2019/0038229 A1 | 2/2019 | Perraut et al. |
| 2019/0049942 A1* | 2/2019 | Dusane ............... B60R 25/25 |
| 2019/0049968 A1 | 2/2019 | Dean et al. |
| 2019/0087691 A1 | 3/2019 | Jelveh |
| 2019/0108407 A1 | 4/2019 | Okayasu |
| 2019/0121356 A1 | 4/2019 | Migneco et al. |
| 2019/0133511 A1 | 5/2019 | Migneco et al. |
| 2019/0168771 A1 | 6/2019 | Migneco et al. |
| 2019/0176837 A1 | 6/2019 | Williams et al. |
| 2019/0193712 A1 | 6/2019 | Kunsanagi et al. |
| 2019/0332902 A1 | 10/2019 | Gallagher et al. |
| 2019/0346843 A1* | 11/2019 | Stark ............... A61B 5/117 |
| 2019/0373038 A1 | 12/2019 | Rider et al. |
| 2019/0373114 A1 | 12/2019 | Gullander |
| 2020/0012403 A1 | 1/2020 | Sculley et al. |
| 2020/0062074 A1 | 2/2020 | Macneille et al. |
| 2020/0155054 A1 | 5/2020 | Slater et al. |
| 2021/0009149 A1 | 1/2021 | Migneco et al. |
| 2021/0031786 A1 | 2/2021 | Gallagher et al. |

FOREIGN PATENT DOCUMENTS

| | | |
|---|---|---|
| CN | 103198617 A | 7/2013 |
| CN | 204147427 U | 2/2015 |
| CN | 104700572 A | 6/2015 |
| CN | 104797484 A | 7/2015 |
| CN | 105595996 A | 5/2016 |
| CN | 106687026 A | 5/2017 |
| CN | 107791893 A | 3/2018 |
| CN | 107949504 A | 4/2018 |
| CN | 108937883 A | 12/2018 |
| CN | 109843174 A | 6/2019 |
| CN | 109927603 A | 6/2019 |
| DE | 10126224 A1 | 12/2002 |
| DE | 102012002037 B4 | 3/2015 |
| DE | 102017111908 A1 | 11/2017 |
| EP | 2308559 A2 | 4/2011 |
| FR | 2880166 A1 | 6/2006 |
| JP | 2010241963 A | 10/2010 |
| JP | 2017021651 A | 1/2017 |
| JP | 2017042544 A | 3/2017 |
| KR | 20140028254 A | 3/2014 |
| WO | 2007090896 A1 | 8/2007 |
| WO | 2015127193 A1 | 8/2015 |
| WO | 2015175435 A1 | 11/2015 |
| WO | 2018156136 A1 | 8/2018 |

(56) References Cited

OTHER PUBLICATIONS

Burgess, M., "This car headrest monitors your brain waves to stop you falling asleep at the wheel", WIRED Online Article, Jan. 15, 2017, 9 pgs.
Lisetti, C., "Affective Intelligent Car Interfaces with Emotion Recognition", In Proceedings of 11th International Conference on Human Computer Interaction, Las Vegas, NV, USA, Jul. 2005.
Ness, J., "Prototype Testing of EEG Headrests", Freer Logic Online Article—Comments Off on Prototype Testing of EEG Headrests, Aug. 3, 2017, 2 pgs.
Stout, Cynthia S., et al., Increasing Accuracy in the Assessment of Motion Sickness: A Construct Methodology, Ames Research Center, NASA Technical Memorandum 108797, Dec. 1993, Moffett Field, California.
The State Intellectual Property Office of the People's Republic of China, Second Office Action for Chinese Application No. 202010376781.X, dated Oct. 10, 2022, 6 pages.
Chinese Office Action dated Apr. 18, 2022 for related Chinese Application No. 202010376781.X; 7 pages.
The State Intellectual Property Office of the People's Republic of China, Notification of Grant for Chinese Application No. 202010376781.X, dated Apr. 2, 2022, 2 pages (including English machine translation).

\* cited by examiner

SEAT SYSTEM AND METHOD OF CONTROL

TECHNICAL FIELD

This disclosure relates to a seat system and a method of control. The method may include assessing a physiological condition of a seat occupant.

BACKGROUND

A vehicle seat with integrated sensors is disclosed in U.S. Pat. No. 8,941,499.

SUMMARY

In at least one embodiment, a method of controlling a seat system is provided. The method may include determining a heart rate, a breathing rate, and a heart rate variability of a seat occupant that is seated in a seat assembly. A physiological condition of the seat occupant may be assessed based on at least two of the heart rate, the breathing rate, and the heart rate variability. A countermeasure may be executed to alter the physiological condition of the seat occupant.

In at least one embodiment, a method of controlling a seat system is provided. The method may include obtaining a pre-exercise data set that may include a heart rate, a breathing rate, and a heart rate variability of a seat occupant that is seated in the seat assembly before the seat occupant begins physical exercise. A post-exercise data set that includes a heart rate, a breathing rate, and a heart rate variability of the seat occupant may be obtained after the seat occupant completes physical exercise. The pre-exercise data set and the post exercise data set may be compared to obtain an analysis result. The analysis result may then be communicated.

In at least one embodiment, a method of controlling a seat system is provided. The method may include detecting a seat occupant that is seated in a seat assembly. A heart rate, a breathing rate, and a heart rate variability of the seat occupant may be determined. The heart rate, breathing rate, and heart rate variability of the seat occupant may be compared to a second data set that may include heart rate data, breathing rate data, and heart rate variability data. At least one of the heart rate, breathing rate, and heart rate variability may be communicated to the seat occupant.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
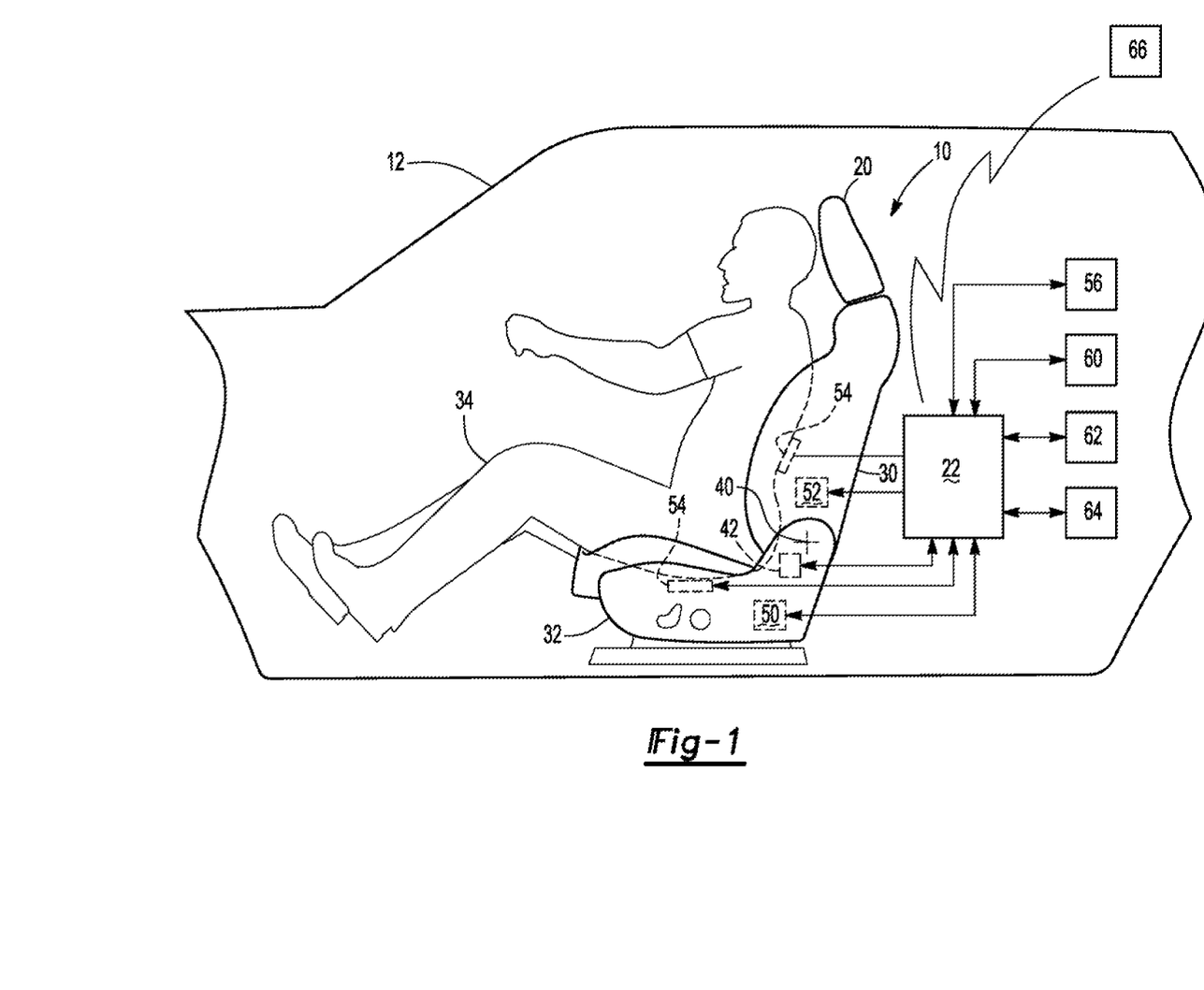
FIG. 1 is a schematic view of a seat system that includes a seat assembly and a seat occupant.

Referring to FIG. 1, an example of a seat system 10 is shown. The seat system 10 may be provided with a vehicle 12, such as a motor vehicle like a car or truck. In at least one configuration, the seat system 10 may include a seat assembly 20 and a control system 22.

The seat assembly 20 may be disposed in the vehicle 12 and may include a seat back 30 and a seat bottom 32.

The seat back 30 may be configured to support the back of a seat occupant 34. The seat back 30 may be rotatable or pivotable about an axis 40 with respect to the seat bottom 32. For example, one or more recliner mechanisms may pivotally connect the seat back 30 to the seat bottom 32. In at power seat assembly, an electric motor 42 may be operable to adjust the inclination angle of the seat back 30 with respect to the seat bottom.

The seat bottom 32 may also be configured to support the seat occupant 34. In a vehicular application, the seat bottom 32 may be mounted to a support surface, such as a vehicle floor.

The seat assembly 20 may include one or more additional components, such as a haptic actuator 50, a massage unit 52, and one or more occupant sensors 54.

The haptic actuator 50 may be configured to vibrate the seat assembly 20 in a manner that may be detectable by the seat occupant 34. A haptic actuator 50 may be provided in the seat back 30, the seat bottom 32, or both. The haptic actuator 50 may be of any suitable type, such as a linear resonant actuator, rotating mass actuator, piezoelectric actuator, or the like.

The massage unit 52 may be configured to massage the seat occupant 34. Massage functionality may be provided in the seat back 30, the seat bottom 32, or both. The massage unit 52 may be of any suitable type. For example, the massage unit 52 may include a plurality of air bladders that may be disposed inside the seat assembly 20 and which may be inflated and deflated to provide a pressing, rolling, or kneading action upon the seat occupant 34.

One or more occupant sensors 54 may be configured to detect or provide a signal indicative of at least one physiological attribute of the seat occupant 34. For instance, the occupant sensors 54 may be configured to detect attributes of the cardiovascular and/or respiratory system of the seat occupant 34 and may provide one or more signals that may be indicative of the heart rate, breathing rate, and heart rate variability of the seat occupant 34. Heart rate (HR) is the number of heartbeats per unit of time, such as heartbeats per minute. Breathing rate (BR) is the number of breaths per unit of time, such as breaths per minute. Heart rate variability (HRV) is the fluctuation in the time interval between adjacent heartbeats. Such signals or data may be based on time-domain measures and/or frequency-domain measures as is known by those skilled in the art. For instance, a time-domain measure of HRV may quantify the amount of variability in measurements of the interbeat interval (IBI), which is the time period between successive heartbeats. A frequency-domain measurement may estimate the distribution of absolute or relative power into four frequency bands.

The occupant sensors 54 may be of any suitable type. As examples, an occupant sensor 54 may be based on or may include radar, a piezoelectric sensor, vision system, sound-based system, or the like. The occupant sensors 54 may be provided in the seat back 30, the seat bottom 32, or both. It is also contemplated that the occupant sensors 54 may be provided inside the vehicle 12 but outside of the seat assembly 20. For instance, an occupant sensor 54 may be mounted in the passenger compartment of the vehicle 12 or may be worn by the seat occupant 34. An occupant sensor 54 that may be worn by a seat occupant 34 may be incorporated in clothing or may be incorporated in a non-clothing accessory (e.g., watch, phone, jewelry, fitness tracker, etc.). Such occupant sensors 54 may communicate wirelessly with the control system 22.

The control system 22 may monitor and control operation of the seat system 10. The control system 22 may include one or more electronic controllers or control modules that may monitor and/or control various components of the seat assembly 20, such as the electric motor 42, haptic actuator 50, and massage unit 52. The control system 22 may also receive a signal or data from the occupant sensors 54 and from a user interface 56.

The user interface 56 may be of any suitable type. For instance, the user interface 56 may be a button, switch, touchpad, keypad, or other input device that may allow the seat occupant 34 to input information or data. The user interface 56 may be part of the vehicle 12 or may be provided with a communication device such as a phone, smartwatch, fitness tracker, computer, or the like. It is also contemplated that the user interface 56 may employ speech recognition, voice commands, or gesture commands.

The control system 22 may also be configured to communicate with and control operation of various components of the vehicle 12, such as an audio system 60, a display 62, and a heating/cooling system 64.

The audio system 60 may provide audible signals to the seat occupant 34. For example, the audio system 60 may include the speakers or sound system that may be provided with the vehicle 12.

The display 62 may provide visual signals or visible information to the seat occupant 34. For example, the display 62 may be provided with the dashboard or instrument panel of the vehicle 12.

The heating/cooling system 64 may be the heating ventilation and air conditioning (HVAC) system of the vehicle 12 that may heat or cool air that may be circulated in the passenger compartment of the vehicle 12. In addition or alternatively, the heating/cooling system 64 may be a heated seat, cooled seat, or heated and cooled seat that may modify the temperature of the seat assembly 20 that is felt by the seat occupant 34.

The control system 22 may also be configured to communicate with devices or systems external to the vehicle 12. For instance, the control system 22 may communicate with an information system 66, such as a computer or database that may be external to the vehicle 12. The information system 66 may include personal devices such as smart watches, phones, and computers and their associated software applications and/or devices or databases controlled by third parties that may collect information regarding the health or physiological condition of the seat occupant 34, including but not limited to health tracking software, medical systems, insurance companies and the like.

Figure 2:
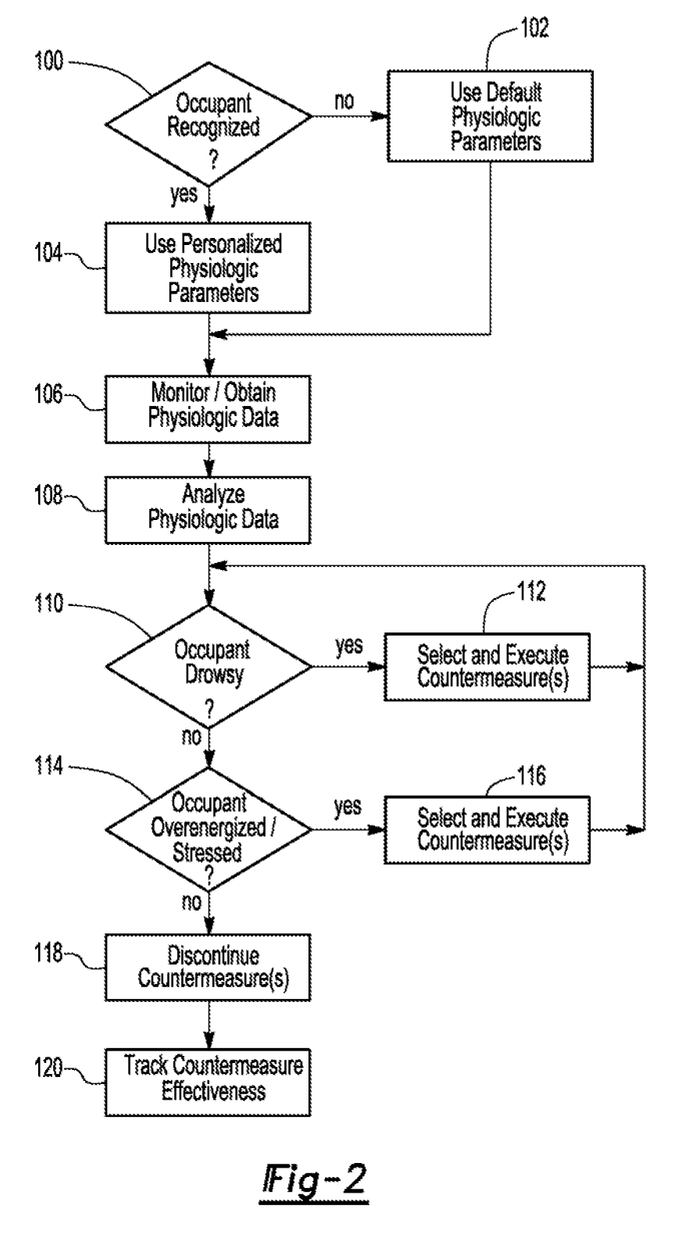
FIG. 2 is a flowchart of a method of control for the seat system associated with assessing and altering a physiological condition of the seat occupant.
Figures 3, 4:
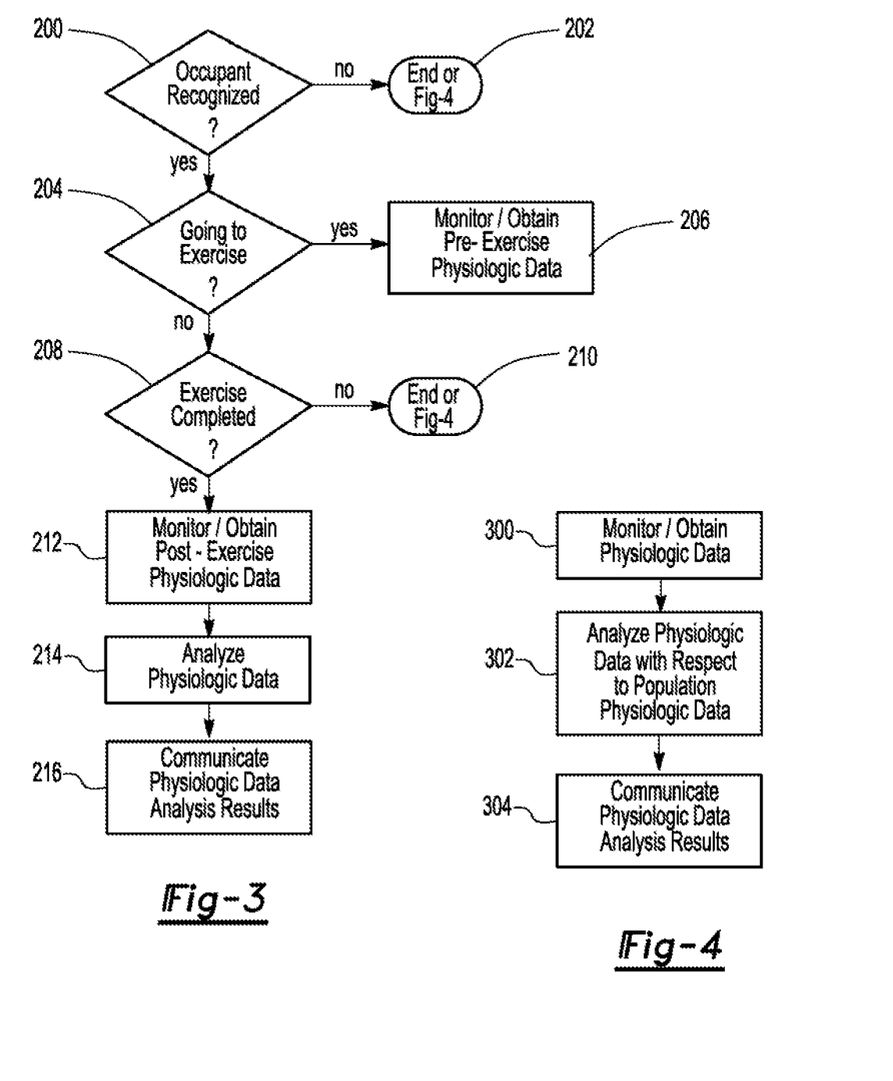
FIG. 3 is a flowchart of a method of control for the seat system related to fitness monitoring of the seat occupant.
FIG. 4 is a flowchart of a method of control for the seat system related to health monitoring of the seat occupant.

Referring to FIGS. 2-4, flowcharts of methods of control of the seat system 10 are shown. As will be appreciated by one of ordinary skill in the art, the flowchart represents control logic which may be implemented or affected in hardware, software, or a combination of hardware and software. For example, the various functions may be affected by a programmed microprocessor. The control logic may be implemented using any of a number of known programming and processing techniques or strategies and is not limited to the order or sequence illustrated. For instance, interrupt or event-driven processing may be employed in real-time control applications rather than a purely sequential strategy as illustrated. Likewise, parallel processing, multi-tasking, or multi-threaded systems and methods may be used.

Control logic may be independent of the particular programming language, operating system, processor, or circuitry used to develop and/or implement the control logic illustrated. Likewise, depending upon the particular programming language and processing strategy, various functions may be performed in the sequence illustrated, at substantially the same time, or in a different sequence while accomplishing the method of control. The illustrated functions may be modified, or in some cases omitted, without departing from the scope intended.

In at least one embodiment, the method may be executed by the control system 22 and may be implemented as a closed loop control system. Moreover, the method may be enabled or disabled based on the operating state of the vehicle 12. For example, the method or control logic may be enabled when the vehicle 12 is turned on, when the vehicle is in motion, or combinations thereof. In addition, the method may be manually activated, such as via an input from the user interface 56.

Referring to FIG. 2, a flowchart of a method of control for the seat system is shown that is associated with assessing and altering a physiological condition of a seat occupant.

At block 100, the method may determine whether a seat occupant is recognized or known. A seat occupant may be recognizable, identifiable or known when the seat occupant has previously occupied the seat assembly 20 or has previously used the seat system 10 and has provided physiological data, such as data associated with heart rate, breathing rate, and/or heart rate variability. A seat occupant may be recognized in various ways. For example, a seat occupant may be recognized based on detection and identification of a key fob, phone, smartwatch, or fitness tracker that is associated with the seat occupant. A seat occupant may also be recognized based on an input from the seat occupant that may be provided via the user interface 56. As another example, the seat occupant may be recognized based on biometric data, such as the height and/or weight of the seat occupant, facial recognition of the seat occupant, fingerprint of the seat occupant, or the like. If the seat occupant is not recognized, then the method may continue at block 102. If the seat occupant is recognized, then the method may continue at block 104.

At block 102, the method may initially use default physiologic parameters or preprogrammed physiologic parameters for subsequent analysis purposes. The method may use such defaults since the seat occupant may not have previously used the seat system 10 and may not have previously provided physiological data that may be used for analysis purposes (i.e., historical data associated with the heart rate, breathing rate, and/or heart rate variability of the seat occupant is not available). Default physiologic parameters or preprogrammed physiologic parameters may include a default baseline heart rate, a default baseline breathing rate, and a default baseline heart rate variability. These defaults may be based on statistics from a known population of people and may provide initial baseline values or baseline ranges as to the normal expected heart rate, breathing rate, and heart rate variability of a typical user. As a more sophisticated example, multiple default values may be preprogrammed in a lookup table and may be associated with gender and age. As such, data indicative of the gender and age of the seat occupant may be communicated to the control system 22 or input by the seat occupant and this data may be used to look up default values that may be stored in the memory of the control system 22 that are associated with gender and/or age ranges to provide default values that may be typical of a larger population of people having these characteristics. The method may continue at block 106.

At block 104, the method may use personalized or historical physiologic parameters based on data previously obtained from the seat occupant for subsequent analysis purposes. These parameters may include a baseline heart rate, a baseline breathing rate, and a baseline heart rate variability that may be calculated or based on data obtained during prior use of the seat system 10. For example, the baseline heart rate may be the average heart rate of the seat occupant that is calculated or based on at least a minimum number of data points and may be calculated using the following formula:

$$HR_{B_i} = \frac{1}{n_{B_i}} \sum_{i=1}^{n_{B_i}} HR_i$$

where:
$HR_{B_i}$ is the initial baseline heart rate,
$n_{B_i}$ is the minimum number of baseline data points required, which may be a predetermined constant of at least 3, and
$HR_i$ is the heart rate at index i.

The baseline breathing rate may be the average breathing rate of the seat occupant based on at least a minimum number of data points and may be calculated using the following formula:

$$BR_{B_i} = \frac{1}{n_{B_i}} \sum_{i=1}^{n_{B_i}} BR_i$$

where:
$BR_{B_i}$ is the initial baseline breathing rate, and
$BR_i$ is the breathing rate at index i.

The baseline heart rate variability may be the average heart rate variability of the seat occupant based on at least a minimum number of data points and may be calculated using the following formula:

$$HRV_{B_i} = \frac{1}{n_{B_i}} \sum_{i=1}^{n_{B_i}} HRV_i$$

where:
$HRV_{B_i}$ is the initial baseline heart rate variability, and
$HRV_i$ is the heart rate variability at index i.

Standard deviations of the initial baseline heart rate, initial baseline breathing rate, and initial baseline heart rate variability may be calculated as follows:

$$\sigma_{HR_{B_i}} = \sqrt{\frac{1}{n_{B_i}} \sum_{i=1}^{n_{B_i}} (HR_i - HR_{B_i})^2}$$

$$\sigma_{BR_{B_i}} = \sqrt{\frac{1}{n_{B_i}} \sum_{i=1}^{n_{B_i}} (BR_i - BR_{B_i})^2}$$

$$\sigma_{HRV_{B_i}} = \sqrt{\frac{1}{n_{B_i}} \sum_{i=1}^{n_{B_i}} (HRV_i - HRV_{B_i})^2}$$

where:

$\sigma_{HR_{B_i}}$ is the baseline heart rate standard deviation, $\sigma_{BR_{B_i}}$ is the baseline breathing rate standard deviation, and $\sigma_{HRV_{B_i}}$ is the baseline heart rate variability standard deviation.

At block 106, physiologic data associated with the seat occupant may be monitored or obtained. Data indicative of the heart rate, breathing rate, and heart rate variability of the seat occupant may be provided by the occupant sensors 54 as previously discussed. Physiologic data may be collected in an ongoing basis so long as the seat occupant is seated in the seat assembly 20. Heart rate data may be used or considered usable to determine the current heart rate or average heart rate when at least three heartbeats are detected. Breathing rate data may be used or considered usable to determine the current breathing rate or average breathing rate after a predetermined number of breaths are detected (e.g., three breaths) or after a predetermined amount of time (e.g., 3 seconds). Heart rate variability data may be user considered usable to determine the current heart rate variability or average heart rate variability after a predetermined period of time (e.g., 15 seconds). Calculations or averages based on the detected data may become more robust over time and as more data is collected.

The baseline values (rates and standard deviations) may be adapted or modified over time and in response to additional use of the seat system 10 by the seat occupant and the collection of additional data. For example, the baseline rates may be changed when the detected heart rate, detected breathing rate, and detected heart rate variability are within plus or minus two standard deviations. For example, the heart rate baseline value may be updated as follows:

$$HR_{B_n} = \frac{1}{n_{B_n}} \sum_{i=1}^{n_{B_n}} HR_i \text{ iff}$$

$$HR_{B_{n-1}} + 2\sigma_{HR_{B_{n-1}}} > HR_i > HR_{B_{n-1}} - 2\sigma_{HR_{B_{n-1}}}$$

where:
$HR_{B_n}$ is the updated (newest) baseline heart rate,
iff is if and only if,
$HR_{B_{n-1}}$ is the previous baseline heart rate, and $\sigma_{HR_{B_{n-1}}}$ is the previous baseline heart rate standard deviation.

The breathing rate baseline value may be updated as follows:

$$BR_{B_n} = \frac{1}{n_{B_n}} \sum_{i=1}^{n_{B_n}} BR_i \quad iff$$

$$BR_{B_{n-1}} + 2\sigma_{BR_{B_{n-1}}} > BR_i > BR_{B_{n-1}} - 2\sigma_{BR_{B_{n-1}}}$$

where:
$BR_{B_n}$ is the updated (newest) baseline breathing rate,
$BR_{B_{n-1}}$ is the previous baseline breathing rate, and $\sigma_{BR_{B_{n-1}}}$ is the previous baseline breathing rate standard deviation.

The heart rate variability baseline value may be updated as follows:

$$HRV_{B_n} = \frac{1}{n_{B_n}} \sum_{i=1}^{n_{B_n}} HRV_i \quad iff$$

$$HRV_{B_{n-1}} + 2\sigma_{HRV_{B_{n-1}}} > HRV_i > HRV_{B_{n-1}} - 2\sigma_{HRV_{B_{n-1}}}$$

where:
$HRV_{B_n}$ is the updated (newest) baseline heart rate variability,
$HRV_{B_{n-1}}$ is the previous baseline heart rate variability, and $\sigma_{HRV_{B_{n-1}}}$ is the previous baseline heart rate variability standard deviation.

The baseline standard deviations may be changed when an updated standard deviation is within plus or minus two standard deviations of the previous standard deviation. Standard deviations that may be associated with the updated baseline heart rate, updated baseline breathing rate, and updated baseline heart rate variability may be calculated as follows:

$$\sigma_{HR_{B_n}} = \sqrt{\frac{1}{n_{B_n}} \sum_{i=1}^{n_{B_n}} (HR_i - HR_{B_n})^2} \quad iff$$

$$HR_{B_{n-1}} + 2\sigma_{HR_{B_{n-1}}} > HR_i > HR_{B_{n-1}} - 2\sigma_{HR_{B_{n-1}}}$$

$$\sigma_{BR_{B_n}} = \sqrt{\frac{1}{n_{B_n}} \sum_{i=1}^{n_{B_n}} (BR_i - BR_{B_n})^2} \quad iff$$

$$BR_{B_{n-1}} + 2\sigma_{BR_{B_{n-1}}} > BR_i > BR_{B_{n-1}} - 2\sigma_{BR_{B_{n-1}}}$$

$$\sigma_{HRV_{B_n}} = \sqrt{\frac{1}{n_{B_n}} \sum_{i=1}^{n_{B_n}} (HRV_i - HRV_{B_n})^2} \quad iff$$

$$HRV_{B_{n-1}} + 2\sigma_{HRV_{B_{n-1}}} > HRV_i > HRV_{B_{n-1}} - 2\sigma_{HRV_{B_{n-1}}}$$

where:

$\sigma_{HR_{B_n}}$ is the updated (newest) baseline heart rate standard deviation, $\sigma_{BR_{B_n}}$ is the updated (newest) baseline breathing rate standard deviation, and $\sigma_{HRV_{B_n}}$ is the updated (newest) baseline heart rate variability standard deviation.

At block 108, the physiologic data may be analyzed to assess the physiological condition of the seat occupant. Such an assessment may be based on at least two of the heart rate, breathing rate, and heart rate variability of the seat occupant. For instance, the assessment may be based on (1) heart rate and breathing rate, (2) heart rate and heart rate variability, (3) breathing rate and heart rate variability, or (4) heart rate, breathing rate, and heart rate variability. Assessing the physiological condition of the seat occupant based on multiple inputs or multiple parameters may provide a more accurate analysis than an analysis based on a single parameter. Moreover, assessing the physiological condition of the seat occupant based on all three inputs may provide a more accurate analysis than an analysis based on two inputs in various situations.

Assessing the physiological condition of the seat occupant may be directed to detecting two primary conditions or states. These conditions or states relate to (1) whether the seat occupant is drowsy and (2) whether the seat occupant is stressed and are further detailed at block 110 and block 114, respectively.

At block 110, the method may determine whether the seat occupant is drowsy (i.e., assessing the physiological condition may be an assessment of drowsiness of the seat occupant or whether the seat occupant may be falling asleep). As one example, the seat occupant may be drowsy when at least two of the following three conditions are met: (a) the current heart rate of the seat occupant is less than the baseline heart rate, (b) the current breathing rate is less than the baseline breathing rate, and (c) the heart rate variability is greater than the baseline heart rate variability. As a more refined example, the baseline heart rate, baseline breathing rate, baseline heart rate variability, or combinations thereof may be adjusted by two standard deviations. For example, the seat occupant may be drowsy when at least two of the following three conditions are met: (a') the heart rate of the seat occupant is less than the baseline heart rate minus two standard deviations of the baseline heart rate, (b') the breathing rate of the seat occupant is less than the baseline breathing rate minus two standard deviations of the baseline breathing rate, and (c') the heart rate variability of the seat occupant is greater than the baseline heart rate variability plus two standard deviations of the baseline heart rate variability. An example based on heart rate, breathing rate, and standard deviation adjustments is as follows:

$$\text{Drowsy iff } HR_t < HR_B - 2\sigma_{HR_B} \text{ and } BR_t < BR_B - 2\sigma_{BR_B}$$

where:
$HR_t$ is the heart rate of the seat occupant over period t,
$HR_B$ is the baseline heart rate,
$\sigma_{HR_B}$ is the baseline heart rate standard deviation,
$BR_t$ is the breathing rate of the seat occupant over period t,
$BR_B$ is the baseline breathing rate, and
$\sigma_{BR_B}$ is the baseline heart breathing rate standard deviation.

A similar computation may be made using baseline heart rate variability and its standard deviation in combination with at least one of the preceding drowsiness calculations for heart rate and breathing rate. If at least two of the three conditions (a), (b), and (c) or (a'), (b'), and (c') are met, then the method may continue at block 112. Otherwise, the method may continue at block 114.

At block 112, one or more countermeasures may be selected and executed to attempt to reduce the drowsiness or increase the alertness of the seat occupant. These countermeasures may include but may not be limited to changing the inclination angle of the seat back 14 (e.g., rotating the seat back to a more upright position) by operating the electric motor 42, providing a tactile sensation to the seat occupant with the haptic actuator 50 (e.g., providing rapid vibration impulses), vigorously massaging the seat occupant with the massage unit 52, providing an audible signal with the audio system 60 (e.g., providing vigorous or upbeat music, increasing the audio volume, providing a warning chime or tone, etc.), providing a visual message with the display 62 (e.g., a warning message or warning indicator), changing the temperature of the seat assembly and/or the passenger compartment with the heating/cooling system 64 (e.g., providing cooled air and/or increasing the airflow rate), providing stimulative pulsed electromagnetic therapy (PEMF) with coils that may be provided with the seat assembly 20, or combinations thereof.

It is contemplated that execution of countermeasures may be sequential or simultaneous. For example, countermeasures may be executed in a predetermined default sequence until drowsiness is alleviated. Such a sequence may include implementing countermeasures that are perceived to be less alarming such as providing an audible signal, changing the temperature, and/or providing PEMF prior to executing other countermeasures that may be perceived to be more alarming, such as changing the seat back inclination angle, haptic impulses, or vigorous massage impulses. It is also contemplated that the countermeasure or countermeasures that are first implemented may be those that were previously successful in reducing the drowsiness or increasing the alertness of the seat occupant during previous iterations of the method. The method may then return to block 110 to assess whether the seat occupant is still drowsy, which may result in block 110 and block 112 being executed in a loop so long as the occupant remains drowsy. It is further contemplated that one or more countermeasures may be executed for a predetermined period of time (e.g., 1 minute) before selecting and implementing a different countermeasure or an additional countermeasure.

At block 114, the method may determine whether the seat occupant is stressed or over energized (i.e., assessing the physiological condition may be an assessment of stress or the stress level of the seat occupant). As one example, the seat occupant may be stressed when at least two of the following three conditions are met: (d) the current heart rate of the seat occupant is greater than the baseline heart rate, (e) the current breathing rate is greater than the baseline breathing rate, and (f) the heart rate variability is less than the baseline heart rate variability. As a more refined example, the baseline heart rate, baseline breathing rate, baseline heart rate variability, or combinations thereof may be adjusted by at least one standard deviation. For example, the seat occupant may be stressed when at least two of the following three conditions are met: (d') the heart rate of the seat occupant is greater than the baseline heart rate plus two standard deviations of the baseline heart rate, (e') the breathing rate of the seat occupant is greater than the baseline breathing rate minus one standard deviations of the baseline breathing rate, and (f') the heart rate variability of the seat occupant is less than the baseline heart rate variability plus two standard deviations of the baseline heart rate variability. An example based on heart rate, breathing rate, and standard deviation adjustments is as follows:

$$\text{Seat occupant is stressed iff } HR_t > HR_B + 2\sigma_{HR_B} \text{ and } BR_t > BR_B - \sigma_{BR_B}$$

where:
$HR_t$ is the heart rate over time period t, and
$BR_t$ is the breathing rate over time period t.

A similar computation may be made using baseline heart rate variability and its standard deviation in combination with at least one of the preceding drowsiness calculations for heart rate and breathing rate. If at least two of the three conditions (d), (e), and (f) or (d'), (e'), and (f') are met, then the method may continue at block 116. Otherwise, the method may continue at block 118.

The method may also be able to assess or determine the type of stress experienced by the seat occupant. For instance, the method may be able to distinguish between physiological stress and psychological stress. As an example, the method may first determine whether a person is undergoing physiological or psychological stress in accordance with the following formula, in which a seat occupant may be stressed when the heart rate of the seat occupant is greater than the baseline heart rate of the seat occupant plus two standard deviations of the baseline heart rate and the breathing rate of the seat occupant is greater than the baseline breathing rate minus one standard deviation of the baseline breathing rate.

If the seat occupant is stressed, then the method may categorize the type of stress as being physical stress or mental stress in accordance with the following formula:

$$\text{Physical stress iff } HR_t > T_p * HR_{max}, \text{ otherwise mental stress}$$

where:
$T_p$ is a threshold percentage multiplier, and
$HR_{max}$ is 220–the age of the seat occupant.

The method may further categorize types of physical stress into multiple types, such as basic physical stress, post-training or post-exercise physical stress, training or exercise physical stress, and high or potentially dangerous stress in accordance with the following formulas:

Basic Physical Stress:

$$HR_P \text{ iff } HR_B+0.5*HRR > HR_t > T_p*HR_{max}$$

where:
$HR_P$ is basic physical stress,
$HR_B$ is the baseline heart rate of the seat occupant,
HRR is the available upper heart rate range and is based on the following formula:

$$HRR = HR_{max} - HR_B$$

where:
$HR_{max}$ is 220–the age of the seat occupant
$HR_t$ is the current heart rate of the seat occupant, $$T_p = T_{p_{min}} \geq \frac{HR_B + 0.5*HRR}{HR_{max}}$$

where:
$T_{p_{min}}$ is a predetermined minimum threshold percentage multiplier

Post-Training Physical Stress ($HR_{Pt}$):

$$HR_{PT} \text{ iff } HR_B+0.7*HRR > HR_t \geq HR_B+0.5*HRR$$

Training (Exercise) Physical Stress ($HR_{Tr}$):

$$HR_{Tr} \text{ iff } HR_B+0.85*HRR \geq HR_t \geq HR_B+0.7*HRR$$

Potentially Dangerous Physical Stress ($HR_D$):

$$HR_D \text{ iff } HR_t > HR_B+0.85*HRR$$

At block 116, one or more countermeasures may be selected and executed to attempt to reduce the stress of the seat occupant or calm the seat occupant. These countermeasures may include but may not be limited to changing the inclination angle of the seat back 14 (e.g., rotating the seat back to a less upright position) by operating the electric motor 42, providing a tactile sensation to the seat occupant with the haptic actuator 50 (e.g., providing slow vibration impulses), massaging the seat occupant in a soothing or non-vigorous manner with the massage unit 52, providing an audible signal with the audio system 60 (e.g., providing soothing music, decreasing the audio volume, etc.), providing a visual message with the display 62 (e.g., a "take a break" message or indicator), providing calming pulsed electromagnetic therapy (PEMF), or combinations thereof.

If the type of stress is identified as being physical stress, then one or more countermeasures may be selected to help cool the seat occupant, such as by operating the heating/cooling system 64 in a cooling mode or operating the massage unit. If the type of stress is identified as being mental stress, then one or more countermeasures may be selected to address the mental state of the seat occupant, such as providing calming music with the audio system 60 or reclining the seat back.

It is contemplated that countermeasures may be implemented sequentially or simultaneously. For example, countermeasures may be executed in a predetermined default sequence as previously discussed. It is also contemplated that the countermeasure or countermeasures that are first implemented may be those that were previously successful in reducing the stress of the seat occupant during previous iterations of the method. The method may then return to block 114 (directly or via block 110) to assess whether the seat occupant remains stressed, which may result in block 114 and block 116 being executed in a loop. It is further contemplated that one or more countermeasures may be executed for a predetermined period of time (e.g., 1 minute) before selecting and implementing a different countermeasure or an additional countermeasure.

At block 118, any active countermeasures are discontinued as the seat occupant is no longer considered or to be drowsy or stressed.

At block 120, the effectiveness of a countermeasure may be tracked. Tracking the effectiveness of a countermeasure may include storing information as to which countermeasure or countermeasures were active prior to discontinuation at block 118. The last countermeasure or combination of countermeasures that were active may be considered to be effective at altering the physiological condition of a particular the seat occupant in the desired manner and thus may be selected as the initial countermeasure or countermeasures employed for that seat occupant the next time that physiological condition is detected to help provide a desired response in a more rapid manner. In addition, tracking the effectiveness of a countermeasure may provide feedback that may help monitor or detect stimulus habituation (i.e., reduced effectiveness of a countermeasure). Stimulus habituation may be indicated by an increase in the amount of time for a countermeasure to be effective as compared to previous times in which the countermeasure was employed. As such, the time between implementing a countermeasure and obtaining a desired physiologic response may be measured and assessed to determine whether there is a trend in the "time to effectiveness" for a particular countermeasure. A countermeasure may be employed when its effectiveness is stable or improving and may be replaced with another countermeasure for a particular seat occupant when its effectiveness is decreasing for that seat occupant.

Referring to FIG. 3, a flowchart of a method of control for the seat system is shown that is associated with fitness monitoring of a seat occupant.

At block 200, the method may determine whether a seat occupant is recognized, identified or known. Block 200 is analogous to block 100 of FIG. 2. If the seat occupant is not recognized, then the method may continue at block 202. If the seat occupant is recognized, then the method may continue at block 204.

At block 202, method may end or may continue at block 300 in FIG. 4 as the remaining steps shown in FIG. 3 are executed when the seat occupant is known or recognized.

At block 204, the method may determine whether the seat occupant is going to exercise. A seat occupant may be going to exercise when the seat occupant is traveling, driving, or is in route to a facility (e.g., gymnasium, fitness center, etc.) in which the seat occupant plans to exercise or work out, is driving to or is in route to a sporting event in which the seat occupant will participate, or the like. The purpose of determining whether the seat occupant is going to exercise in the near future is so that physiological data can be collected prior to exercising or completing an exercise routine for later use as a basis of comparison. A determination as to whether seat occupant is going to exercise may be based on a user input (e.g., an input made with the user interface 56 such as a voice command or input made with a button, switch or the like) or information from a phone-based or vehicle-based navigation system that indicates that the destination of the vehicle is a gymnasium or fitness center. If the seat occupant is going to exercise or is traveling to a location where he/she will exercise, then the method may continue at block 206. If the seat occupant is not going to exercise or traveling to exercise, then the method may continue at block 208.

At block 206, pre-exercise physiologic data associated with the seat occupant may be monitored or obtained. Block 206 may be analogous to block 106 of FIG. 2. As such, data indicative of the heart rate, breathing rate, and heart rate variability of the seat occupant may be obtained as previously discussed. This data may be stored in memory by the control system 22 for future use. In addition, the control system 22 may measure the amount of time during which pre-exercise physiologic data is obtained to help assess whether this data may provide a meaningful basis of comparison. For instance, the method may be configured such that pre-exercise physiologic data must be collected for a predetermined period of time (e.g., at least five minutes) to be used as a basis of comparison or analysis.

At block 208, the method may determine whether the seat occupant has completed exercising. The purpose of determining whether the seat occupant has completed exercising is to delineate between a pre-exercise state and a post-exercise state. A determination as to whether the seat occupant has completed exercising may be based on a user input as previously discussed with respect to block 204 or information from a phone-based or vehicle-based navigation system that indicates that the vehicle is leaving a gymnasium or fitness center. The determination as to whether the seat occupant has completed exercising or user input may be made after the seat occupant has returned to the vehicle, such as for traveling home or to another destination. If the seat occupant has not completed exercise, then the method may continue at block 210. If the seat occupant has completed exercising, then the method may continue at block 212.

At block 210, the method may end or continue at block 300 in FIG. 4 as the seat occupant is either (1) not currently involved in fitness related activities (e.g., was not going to exercise at block 204 and thus cannot complete exercising at block 208) or (2) has not completed exercising or provided in associated input that indicates that exercising is complete.

At block 212, post-exercise physiologic data associated with the seat occupant may be monitored or obtained. Block 212 may be similar to block 206 in that data indicative of the heart rate, breathing rate, and heart rate variability of the seat occupant may be obtained. This data may be obtained for a predetermined period of time (e.g., less than two minutes) when the vehicle is stationary or a drive gear ratio is not engaged (i.e., the vehicle is not in drive or reverse) to help isolate a fitness assessment from stress or exertion that may be due to or in response to driving the vehicle. Alternatively or in addition, data may also be obtained while the vehicle is in motion, which may help further evaluate the fitness level or recovery rate of the seat occupant.

At block 214, the pre-exercise physiologic data and the post-exercise physiologic data may be analyzed. Analysis may include comparing the pre-exercise and post-exercise heart rate data, breathing rate data, heart rate variability data, or combinations thereof. Post-exercise physiologic data may be compared to pre-exercise physiologic data if the pre-exercise physiologic was collected for a predetermined period of time as previously discussed with respect to block 206. Analysis of the post exercise physiologic data may also include determining, calculating, or deriving other attributes from the collected data, such as a maximum heart rate, minimum heart rate, heart rate range, maximum breathing rate, minimum breathing rate, breathing rate range, maximum heart rate variance, minimum heart rate variance, maximal oxygen uptake, or the like.

At block 216, the physiologic data analysis results may be communicated. Data analysis results may be communicated with the seat occupant, such as via the display 62. Information that may be provided may include the absolute or relative values of the attributes discussed in block 214 (e.g., pre-exercise data and/or post exercise data), plots of those attributes over time to show trends, rates of change over time, and the like. Data analysis results may also be communicated outside of the vehicle (if authorized by the seat occupant), such as to fitness tracking devices or software or to third parties such as health providers or health insurance providers.

Referring to FIG. 4, a flowchart of a method of control for the seat system is shown that is related to health monitoring of a seat occupant. Unlike FIG. 3, the method in FIG. 4 may be employed when a seat occupant is not recognized and may not provide fitness monitoring that is based on pre-exercise and post-exercise data. The method in FIG. 4 may be employed in conjunction with the methods of FIGS. 2 and 3 or independently from the methods of FIGS. 2 and 3.

At block 300, physiologic data associated with the seat occupant may be monitored or obtained. Block 300 may be analogous to block 106 of FIG. 2. As such, data indicative of the heart rate, breathing rate, and heart rate variability of the seat occupant may be obtained as previously discussed.

At block 302, the physiologic data obtained at block 300 may be analyzed with respect to population physiologic data. For instance, preprogrammed physiologic parameters based on data and statistics from a known population of people may provide values or ranges as to the "normal" or expected heart rate, breathing rate, and heart rate variability of a typical user. As a more sophisticated example, multiple values or ranges may be preprogrammed in a lookup table and may be associated with gender and age. As such, data indicative of the gender and age of the seat occupant may be communicated to the control system 22 or input by the seat occupant and this data may be used to look up values or ranges that are associated with gender and/or age ranges to provide expected or average values or ranges as to the heart rate, breathing rate, and heart rate variability that may be typical of a larger population of people having these characteristics. These population-based values or ranges may be used as a basis of comparison for the physiologic data obtained at block 300.

At block 304, the physiologic data analysis results may be communicated. Data analysis results may be communicated with the seat occupant, such as via the display 62. Information that may be provided may include the absolute or relative values of the attributes discussed in block 300 and/or block 302 (e.g., a comparison of the heart rate, breathing rate, and/or heart rate variability of the seat occupant with respect to corresponding population-based values or ranges of these attributes), thereby providing a basis of assessing the health of the seat occupant as compared to the population that may be representative of the seat occupant. For instance, the heart rate of the seat occupant in the expected or average heart rate of correspond population-based value may be displayed or plotted via the display 62 and thus communicated to the seat occupant. Similar information may be displayed or plotted based on the breathing rate and heart rate variability of the seat occupant with respect to corresponding population-based values or ranges. Data analysis results may also be communicated outside of the vehicle (if authorized by the seat occupant), such as via a wireless communication link to fitness tracking devices or software or to third parties such as health providers or health insurance providers.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of controlling a seat system, comprising:
determining, based on processing of sensory data measured by one or more occupant sensors within a vehicle, a heart rate, a breathing rate, and a heart rate variability of a seat occupant that is seated in a seat assembly of the vehicle;
assessing a physiological condition of the seat occupant based on at least two of: the heart rate, the breathing rate, and the heart rate variability; and
executing a sequence of countermeasures to alter the physiological condition of the seat occupant by implementing a first set of countermeasures which are perceived to be less alarming to the seat occupant and implementing a second set of countermeasures followed by the first set of countermeasures, wherein the second set of countermeasures are perceived to be more alarming to the seat occupant than the first set of countermeasures,
wherein the first set of countermeasures comprises at least one of: (a) providing an audible signal to the seat occupant, (b) changing temperature experienced by the seat occupant, and (c) providing stimulative pulsed electromagnetic therapy (PEMF) to the seat occupant, and
wherein the second set of countermeasures comprises at least one of, (a) changing inclination angle of seat back of the seat, (b) providing a haptic impulse to the seat occupant, and (c) providing a massage impulse to the seat occupant.

2. The method of claim 1, wherein execution of the sequence of countermeasures is subsequently terminated when at least two of the following three conditions are met:
(d) the heart rate is greater than a baseline heart rate,
(e) the breathing rate is greater than a baseline breathing rate, and
(f) the heart rate variability is less than a baseline heart rate variability.

3. The method of claim 2, wherein a second countermeasure of the sequence of countermeasures is executed when a first countermeasure of the sequence of countermeasures is not terminated within a predetermined period of time.

4. The method of claim 1, wherein execution of the sequence of countermeasures is subsequently terminated when at least two of the following three conditions are met:
(d) the heart rate is not less than a baseline heart rate minus two standard deviations of the baseline heart rate,
(e) the breathing rate is not less than a baseline breathing rate minus two standard deviations of the baseline breathing rate, and
(f) the heart rate variability is not greater than a baseline heart rate variability plus two standard deviations of the baseline heart rate variability.

5. The method of claim 1, wherein assessing the physiological condition of the seat occupant further comprises an assessment of stress and the sequence of countermeasures is executed when at least two of the following three conditions are met:
(a) the heart rate is greater than a baseline heart rate,
(b) the breathing rate is greater than a baseline breathing rate, and
(c) the heart rate variability is less than a baseline heart rate variability.

6. The method of claim 1, further comprising:
determining, based on an input by the seat occupant, whether the seat occupant is going to exercise;
obtaining a pre-exercise data set that includes a first measurement of heart rate, a first measurement of breathing rate, and a first measurement of heart rate variability of a seat occupant that is seated in a seat assembly before the seat occupant begins physical exercise;
determining whether the seat occupant has completed exercise;
obtaining a post-exercise data set that includes a second measurement of heart rate, a second measurement of breathing rate, and a second measurement of heart rate variability of the seat occupant after the seat occupant completes physical exercise;
comparing the pre-exercise data set and the post-exercise data set to obtain an analysis result; and
communicating the analysis result.

7. The method of claim 1, wherein assessing the physiological condition of the seat occupant comprises an assessment of drowsiness and the sequence of countermeasures is executed when at least two of the following three conditions are met:
(a) the heart rate is less than a baseline heart rate minus two standard deviations of the baseline heart rate,
(b) the breathing rate is less than a baseline breathing rate minus two standard deviations of the baseline breathing rate, and
(c) the heart rate variability is greater than a baseline heart rate variability plus two standard deviations of the baseline heart rate variability.

8. The method of claim 1, wherein the first set of countermeasures is executed based on the first set of countermeasures has proven successful in alarming the seat occupant as determined from previous sensory data measured by the one or more occupant sensor.

9. A seat system, comprising:
at least one occupant sensor communicatively coupled to a seat assembly of a seat, the occupant sensor configured to provide a signal indicative of a physiological condition of a seat occupant;
a processor communicatively coupled to the occupant sensor, wherein the processor is configured to:
determine based on processing sensory data by the occupant sensor, a heart rate, a breathing rate, and a heart rate variability of the seat occupant that is seated in the seat assembly;
assess a physiological condition of the seat occupant based on at least two of the heart rate, the breathing rate, and the heart rate variability; and
execute a sequence of countermeasures to alter the physiological condition of the seat occupant, wherein the sequence of countermeasures is executed by implementing a first set of countermeasures which are perceived to be less alarming to the seat occupant and implementing a second set of countermeasures followed by the first set of countermeasures, wherein the second set of countermeasures are perceived to be more alarming to the seat occupant than the first set of countermeasures,
wherein the first set of countermeasures comprises at least one of: (a) providing an audible signal to the seat occupant, (b) changing temperature experienced by the seat occupant, and (c) providing stimulative pulsed electromagnetic therapy (PEMF) to the seat occupant, and wherein the second set of countermeasures comprises at least one of, (a) changing inclination angle of seat back of the seat, (b) providing a haptic impulse to the seat occupant, and (c) providing a massage impulse to the seat occupant.

10. The seat system of claim 9, wherein the processor is further configured to: cause termination of the execution of the sequence of countermeasures when the heart rate is not greater than the baseline heart rate plus two standard deviations of the baseline heart rate, and the breathing rate is not greater than the baseline breathing rate minus one standard deviation of the baseline breathing rate.

11. The seat system of claim 9, wherein the processor is configured to assess the physiological condition of the seat occupant including characterizing stress as physical stress or psychological stress based on the heart rate and an age of the seat occupant.

12. The seat system of claim 9, wherein assessing the physiological condition of the seat occupant comprises an assessment of stress and the sequence of countermeasures is executed when at least two of the following three conditions are met:
   (a) the heart rate is greater than a baseline heart rate plus two standard deviations of the baseline heart rate,
   (b) the breathing rate is greater than a baseline breathing rate minus one standard deviation of the baseline breathing rate, and
   (c) the heart rate variability is greater than a baseline heart rate variability plus two standard deviations of the baseline heart rate variability.

13. The seat system of claim 9, wherein the processor is further configured to determine the physiological condition of the seat occupant comprising an assessment of drowsiness and the sequence of countermeasures is executed when at least two of the following three conditions are met:
   (a) the heart rate is less than a baseline heart rate minus two standard deviations of the baseline heart rate,
   (b) the breathing rate is less than a baseline breathing rate minus two standard deviations of the baseline breathing rate, and
   (c) the heart rate variability is greater than a baseline heart rate variability plus two standard deviations of the baseline heart rate variability.

14. The seat system of claim 9, wherein the processor is further configured to determine the physiological condition of the seat occupant comprising an assessment of stress and the sequence of countermeasures is executed when at least two of the following three conditions are met:
   (a) the heart rate is less than a baseline heart rate minus two standard deviations of the baseline heart rate,
   (b) the breathing rate is less than a baseline breathing rate minus two standard deviations of the baseline breathing rate, and
   (c) the heart rate variability is greater than a baseline heart rate variability plus two standard deviations of the baseline heart rate variability.

15. The seat system of claim 9, further comprising:
a heating ventilation and air conditioning (HVAC) system communicatively coupled to the processor, wherein the processor is configured to command the HVAC system to modify temperature of the seat assembly that is felt by the seat occupant, in response to the assessment of the physiological condition of the seat occupant.

16. The seat system of claim 9, further comprising:
a haptic actuator provided in the seat assembly, wherein the haptic actuator is communicatively coupled to the processor and wherein the processor is configured to command the haptic actuator to cause vibration of the seat assembly in response to the assessment of the physiological condition of the seat occupant.

17. The seat system of claim 9, further comprising:
a massage unit comprising a plurality of air bladders disposed in the seat assembly, wherein the massage unit is communicatively coupled to the processor and wherein the processor is configured to command the massage unit to provide massage to the seat occupant, in response to the assessment of the physiological condition of the seat occupant.

18. The seat system of claim 9, further comprising:
a plurality of coils disposed in the seat assembly, the plurality of coils communicatively coupled to the processor and wherein the processor is configured to command execution of stimulative pulsed electromagnetic therapy (PEMF) through the plurality of coils to the seat occupant, in response to the assessment of the physiological condition of the seat occupant.

19. The seat system of claim 9, wherein the first set of countermeasures is executed based on the first set of countermeasures has proven successful in alarming the seat occupant as determined from previous sensory data measured by the one or more occupant sensor.

* * * * *